(12) United States Patent
Kang et al.

(10) Patent No.: US 10,342,496 B2
(45) Date of Patent: Jul. 9, 2019

(54) DEVICE AND SYSTEM FOR MEASURING BIOMETRIC INFORMATION

(71) Applicant: SAMSUNG ELECTRONICS CO., LTD., Suwon-si (KR)

(72) Inventors: Jaemin Kang, Seoul (KR); Yongjoo Kwon, Yongin-si (KR); Sunkwon Kim, Suwon-si (KR); Younho Kim, Hwaseong-si (KR); Sangyun Park, Hwaseong-si (KR)

(73) Assignee: SAMSUNG ELECTRONICS CO., LTD., Suwon-si (KR)

( * ) Notice: Subject to any disclaimer, the term of this patent is extended or adjusted under 35 U.S.C. 154(b) by 690 days.

(21) Appl. No.: 14/809,623

(22) Filed: Jul. 27, 2015

(65) Prior Publication Data

US 2016/0220194 A1 Aug. 4, 2016

(30) Foreign Application Priority Data

Jan. 30, 2015 (KR) .......................... 10-2015-0015575

(51) Int. Cl.
| | | |
|---|---|---|
| *A61B 5/00* | (2006.01) | |
| *A61B 5/0215* | (2006.01) | |
| *A61B 5/021* | (2006.01) | |

(52) U.S. Cl.
CPC ........ *A61B 5/7278* (2013.01); *A61B 5/02154* (2013.01); *A61B 5/02108* (2013.01); *A61B 2503/10* (2013.01)

(58) Field of Classification Search
CPC .............. A61B 5/7278; A61B 5/02108; A61B 5/02154; A61B 2503/10
See application file for complete search history.

(56) References Cited

U.S. PATENT DOCUMENTS

| | | | | |
|---|---|---|---|---|
| 5,265,011 A | * | 11/1993 | O'Rourke .............. | A61B 5/021 128/920 |
| 2009/0326386 A1 | * | 12/2009 | Sethi ...................... | A61B 5/021 600/480 |
| 2013/0109947 A1 | * | 5/2013 | Wood ................... | A61B 5/0095 600/407 |
| 2014/0012510 A1 | | 1/2014 | Mensinger et al. | |
| 2014/0276145 A1 | | 9/2014 | Banet et al. | |
| 2015/0374296 A1 | * | 12/2015 | Baru .................... | A61B 5/0205 600/377 |

FOREIGN PATENT DOCUMENTS

| | | |
|---|---|---|
| KR | 1020080090194 A | 10/2008 |
| KR | 1020120047878 A | 5/2012 |

* cited by examiner

*Primary Examiner* — Peter Luong
(74) *Attorney, Agent, or Firm* — Sughrue Mion, PLLC

(57) ABSTRACT

A biometric information measuring device includes a pulse wave measuring module configured to measure pulse waves by emitting light toward a target object and sensing light reflected from the target object; a communication module configured to obtain calibration information from a remote calibration server; and a biometric information analyzing module configured to analyze biometric information based on the measured pulse waves and the calibration information. The calibration information indicates biometric information measurement variables of a plurality of subjects.

16 Claims, 10 Drawing Sheets

DEVICE AND SYSTEM FOR MEASURING BIOMETRIC INFORMATION

CROSS-REFERENCE TO RELATED APPLICATION

This application claims priority from Korean Patent Application No. 10-2015-0015575, filed on Jan. 30, 2015, in the Korean Intellectual Property Office, the disclosure of which is incorporated herein by reference in its entirety.

BACKGROUND

1. Field

Apparatuses and methods consistent with exemplary embodiments relate to biometric information measuring devices and biometric information measuring systems.

2. Description of the Related Art

Along with increased interests on health, various types of biometric information measuring devices are being developed. Particularly, along with popularization of various types of wearable devices that may be worn by a target object, devices for health care are being developed.

Generally, methods for detecting biometric information, such as pulse waves, may include invasive methods and non-invasive methods. Recently, non-invasive methods of easily detecting pulse waves without inflicting pain to a target object are widely used.

For accurate pulse wave analysis (PWA), it is necessary to obtain information based on optical signals or pressure signals at a fixed location on the body surface. Biometric information regarding a target object may be obtained based on such information, where various methods are used to reduce measurement errors.

SUMMARY

One or more exemplary embodiments provide biometric information measuring devices and biometric information measuring systems.

According to an aspect of an exemplary embodiment, a biometric information measuring device includes a pulse wave measuring module configured to measure pulse waves by emitting a light to a target object and sensing a light from the target object; a communication module configured to obtain calibration information from a remote calibration server; and a biometric information analyzing module configured to analyze biometric information based on the measured pulse waves and the calibration information. The calibration information indicates biometric information measurement variables of a plurality of subjects.

The biometric information analyzing module includes a feature point extracting module configured to analyze the measured pulse waves to extract designated feature points therefrom; and a blood pressure calculator configured to calculate a blood pressure by using a blood pressure estimating equation and the feature points.

The calibration server includes a database in which parameters regarding relationships between reference pulse waves and reference blood pressures are stored; and a blood pressure estimating equation calculator configured to calculate the blood pressure estimating equation by using the database.

The blood pressure calculator receives the blood pressure estimating equation from the calibration server.

The biometric information measuring device further includes a reference blood pressure measuring module which measures a blood pressure of a target object using a direct method.

The biometric information measuring device further includes a blood pressure-pulse wave data set extracting module which extracts parameters regarding relationships between pulse waves and blood pressures from the pulse waves measured by the pulse wave measuring module and blood pressure measured by the reference blood pressure measuring module.

The calibration server receives the parameters from the blood pressure-pulse wave data set extracting module and updates the database.

The biometric information measuring device further includes a local database in which the parameters regarding the relationships between the reference pulse waves and the reference blood pressures are stored.

The biometric information measuring device further includes a blood pressure estimating equation calculator configured to update the local database by using the parameters extracted by the blood pressure-pulse wave data set extracting module and calculate the blood pressure estimating equation by using the updated local database.

The blood pressure estimating equation calculator receives data of the database in the calibration server to update the local database and updates the blood pressure estimating equation by using the updated local database.

The pulse wave measuring module, the biometric information analyzing module, and the communication module are arranged in a main body of the biometric information measuring device, and the reference blood pressure measuring module is connected to the main body.

The main body is wearable on the target object.

The biometric information measuring device is wearable on the target object.

According to another aspect of an exemplary embodiment, there is provided a biometric information measuring system including: a biometric information measuring device includes a pulse wave measuring module which measures pulse waves by emitting a light to a target object and sensing a light reflected from the target object; a biometric information analyzing module which analyzes biometric information based on the pulse waves measured by the pulse wave measuring module; and a communication module which obtains calibration information used to analyze the biometric information by the biometric information analyzing module; a calibration server which communicates with the communication module of the biometric information measuring device and transmits the calibration information to the biometric information measuring device.

The calibration server includes a database which stores parameters regarding relationships between reference pulse waves and reference blood pressures; and a blood pressure estimating equation calculator which calculates a blood pressure estimating equation used for analyzing the biometric information by using the database.

The calibration information is at least one of the parameters stored in the database and the blood pressure estimating equation.

The biometric information measuring system further includes a reference blood pressure measuring module which directly measures a blood pressure of a target object.

The biometric information measuring module further includes a blood pressure-pulse wave data set extracting module which extracts parameters regarding relationships between pulse waves and blood pressures from pulse waves measured by the pulse wave measuring module and the blood pressure measured by the reference blood pressure measuring module.

The calibration server receives the parameters from the blood pressure-pulse wave data set extracting module, updates the database by using the same, and updates the blood pressure estimating equation by using the updated database.

The pulse wave measuring module, the biometric information analyzing module, and the communication module are arranged in a main body of the biometric information measuring device, and the reference blood pressure measuring module is connected to the main body.

BRIEF DESCRIPTION OF THE DRAWINGS

The above and/or other aspects will be more apparent by describing certain exemplary embodiments, with reference to the accompanying drawings, in which.

DETAILED DESCRIPTION

Figure 1:
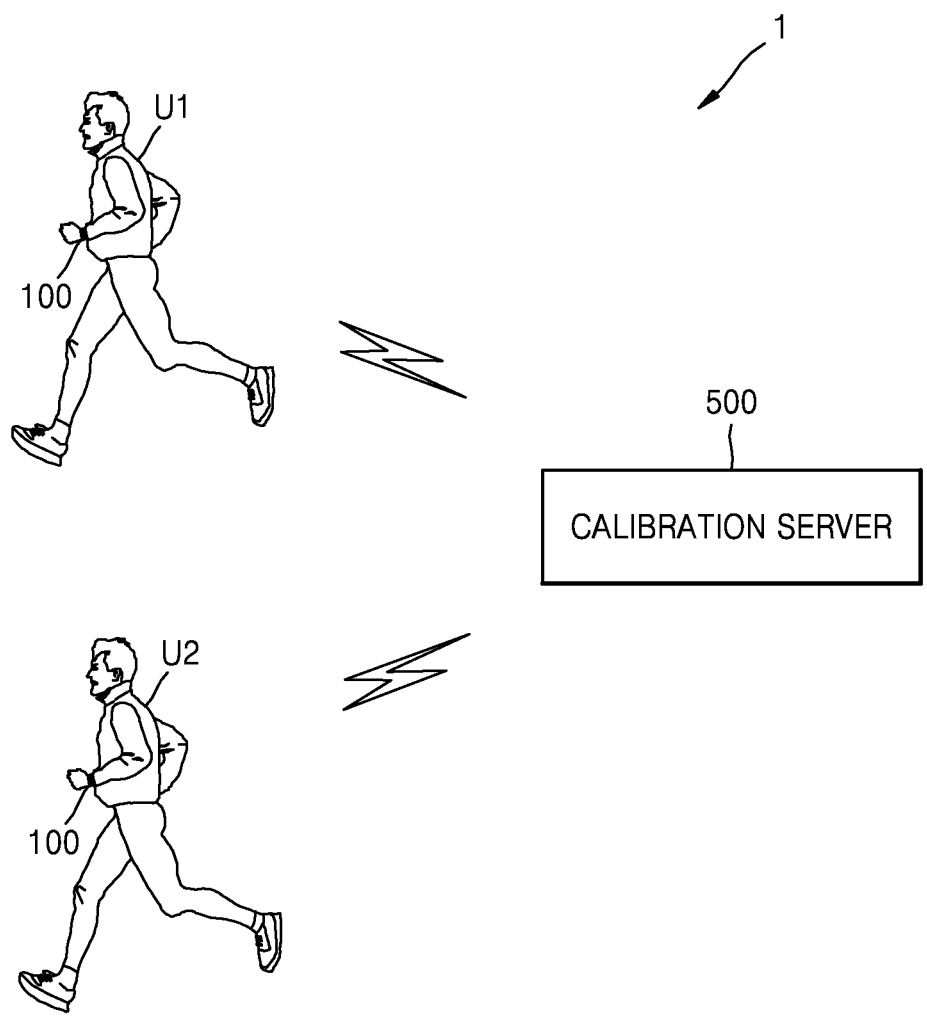
FIG. 1 is a diagram showing a biometric information measuring system according to an exemplary embodiment.

Exemplary embodiments are described in greater detail below with reference to the accompanying drawings.

In the following description, like drawing reference numerals are used for like elements, even in different drawings. The matters defined in the description, such as detailed construction and elements, are provided to assist in a comprehensive understanding of the exemplary embodiments. However, it is apparent that the exemplary embodiments can be practiced without those specifically defined matters. Also, well-known functions or constructions are not described in detail since they would obscure the description with unnecessary detail.

It will be understood that, although the terms first, second, third, etc., may be used herein to describe various elements, components, regions, layers and/or sections, these elements, components, regions, layers and/or sections should not be limited by these terms.

The terminology used herein is for the purpose of describing particular exemplary embodiments only and is not intended to be limiting of the invention. As used herein, the singular forms "a", "an" and "the" are intended to include the plural forms as well, unless the context clearly indicates otherwise. It will be further understood that the terms "comprises" and/or "comprising," when used in this specification, specify the presence of stated features, integers, steps, operations, elements, and/or components, but do not preclude the presence or addition of one or more other features, integers, steps, operations, elements, components, and/or groups thereof.

In addition, the terms "-er", "-or", and "module" described in the specification mean modules for processing at least one function and operation and can be implemented by hardware components or software components and combinations thereof.

FIG. 1 is a diagram showing a biometric information measuring system 1 according to an exemplary embodiment.

The biometric information measuring system 1 includes a plurality of biometric information measuring modules 100 and a calibration server 500. The plurality of biometric information measuring modules 100 may be devices to be respectively worn by different users and to measure biometric information of the respective users wearing the biometric information measuring modules 100. Although FIG. 1 shows that the biometric information measuring system 1 is a wrist-wearing type, the present embodiment is not limited thereto.

The biometric information measuring modules 100 may be indirect blood pressure measuring devices. In other words, the biometric information measuring modules 100 may be a cuffless-type blood pressure measuring device, which emits a light to bodies of users U1 and U2 wearing the biometric information measuring modules 100, measuring pulse waves by sensing reflected or diffused lights, and measuring biometric information, such as blood pressures, by analyzing the pulse waves.

Accuracy of indirectly measured values of blood pressures may significantly depend on calibration information. For example, calibration information may include blood pressure values measured using direct methods, which are more reliable than indirect methods, and parameters related to pulse waves corresponding thereto. Calibration information may be a database in which waveforms of various pulse waves and blood pressure values corresponding thereto are stored. Alternatively, calibration information may be a blood pressure estimating equation calculated based on such a database.

According to the present exemplary embodiment, a plurality of users may update the calibration information, and access the updated calibration information for analysis of biometric information. A plurality of users and the calibration server 500 may exchange calibration information via a social network service (SNS). For example, users U1 and U2 may update calibration information in the calibration server 500 and receive the updated calibration information from the calibration server 500. Although FIG. 1 shows communication between the two users U1 and U2, the number of users is not limited thereto. Based on the biometric information measuring system 1, a user using the biometric information measuring module 100 may utilize biometric information updated by the corresponding user and/or a plurality of other users whenever necessary, and thus highly accurate biometric information may be obtained.

Figure 2:
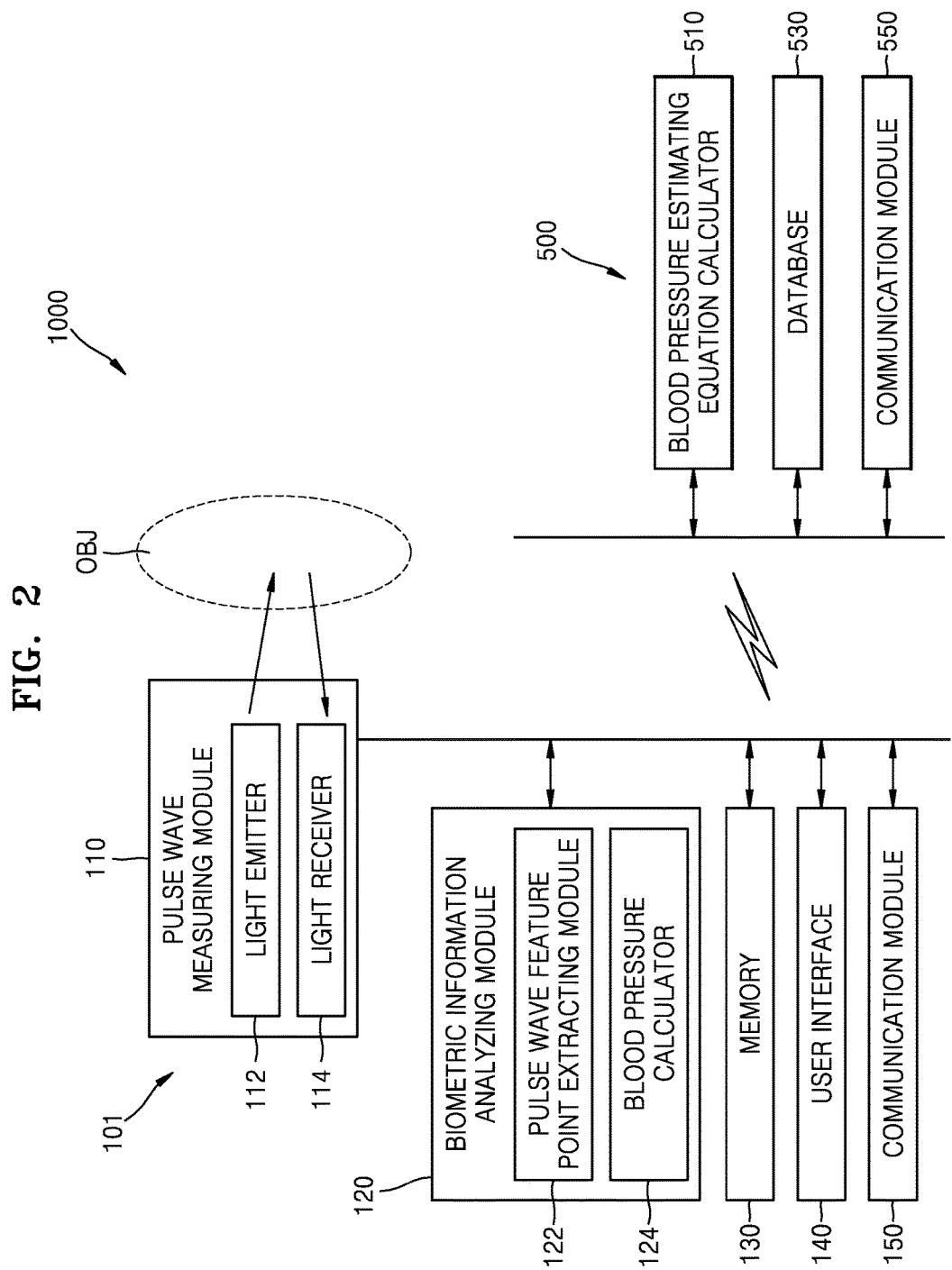
FIG. 2 is a schematic block diagram showing a biometric information measuring system according to another exemplary embodiment.
Figure 3A:
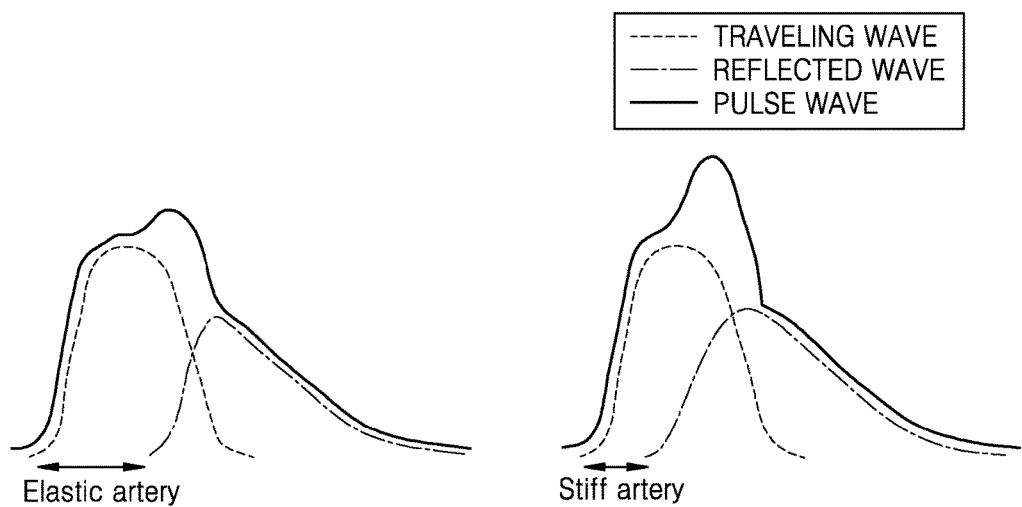
FIGS. 3A through 3C are diagrams showing examples of formation, shapes, and meanings of pulse waves measured by a biometric information measuring module of the biometric information measuring system.
Figure 3B:
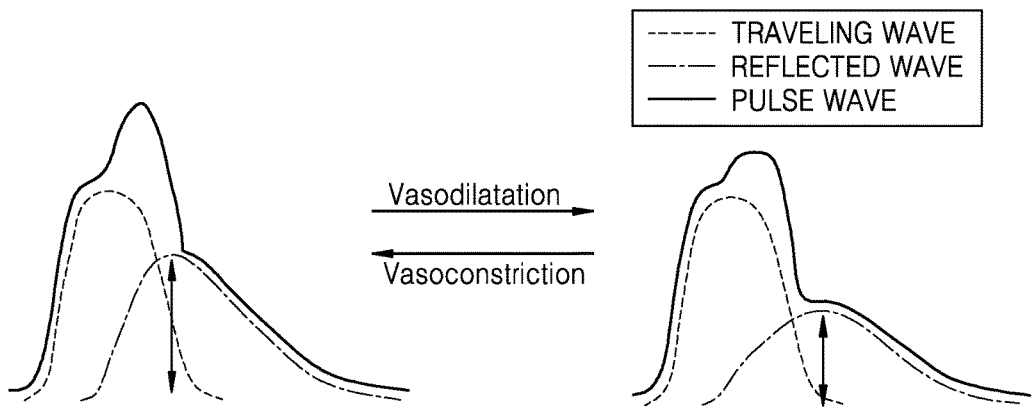
Figure 3C:
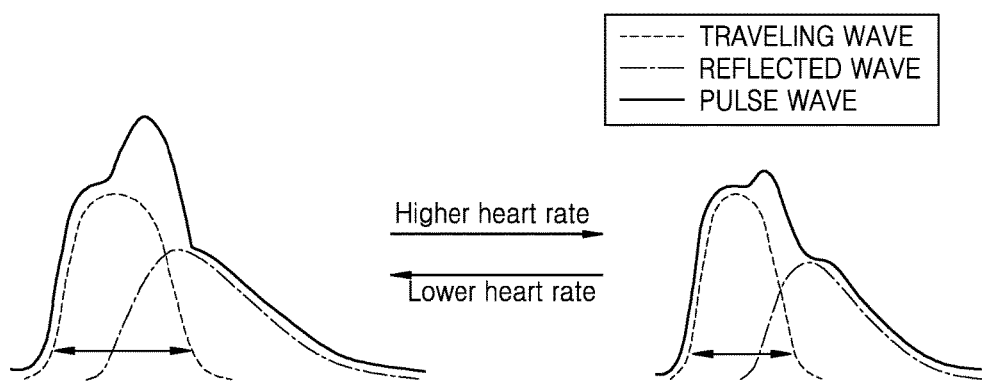
Figure 4:
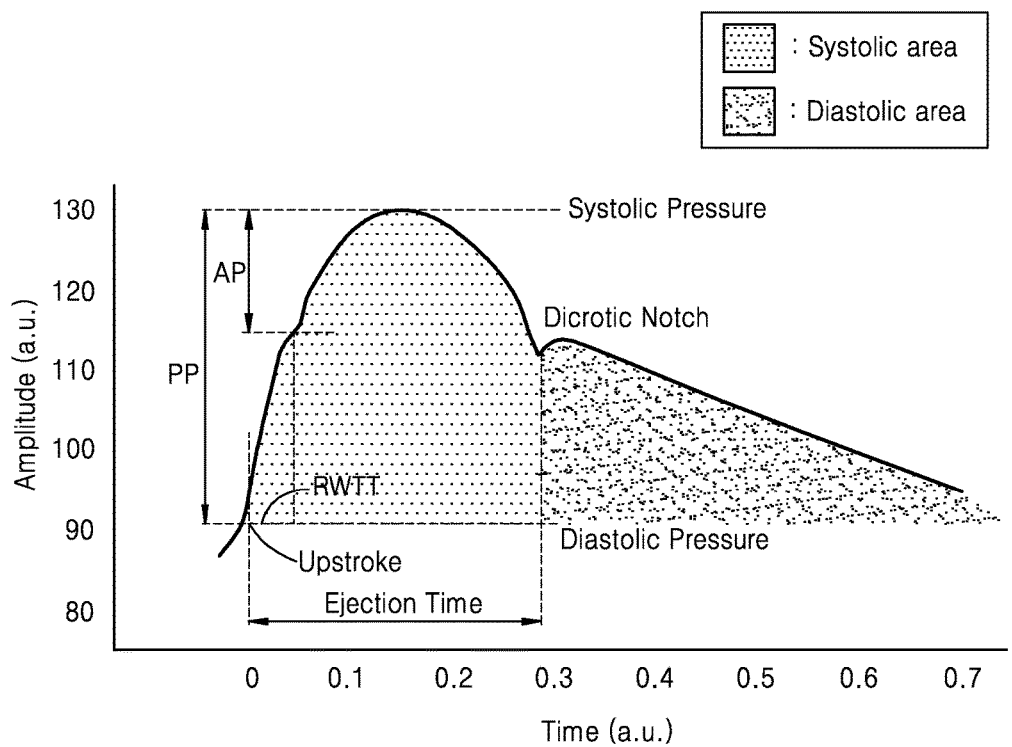
FIG. 4 is a diagram showing an example of biometric information that may be extracted from waveforms of pulse waves.
Figure 5:
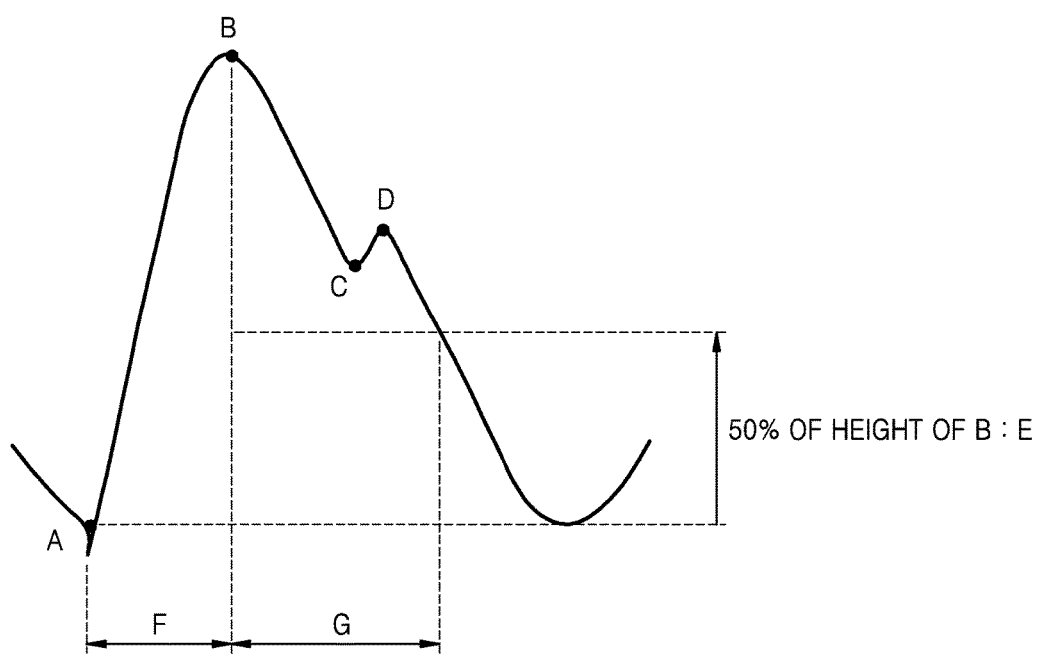
FIG. 5 is a diagram showing pulse wave feature points that may be extracted from waveforms of pulse waves.
Figure 6:
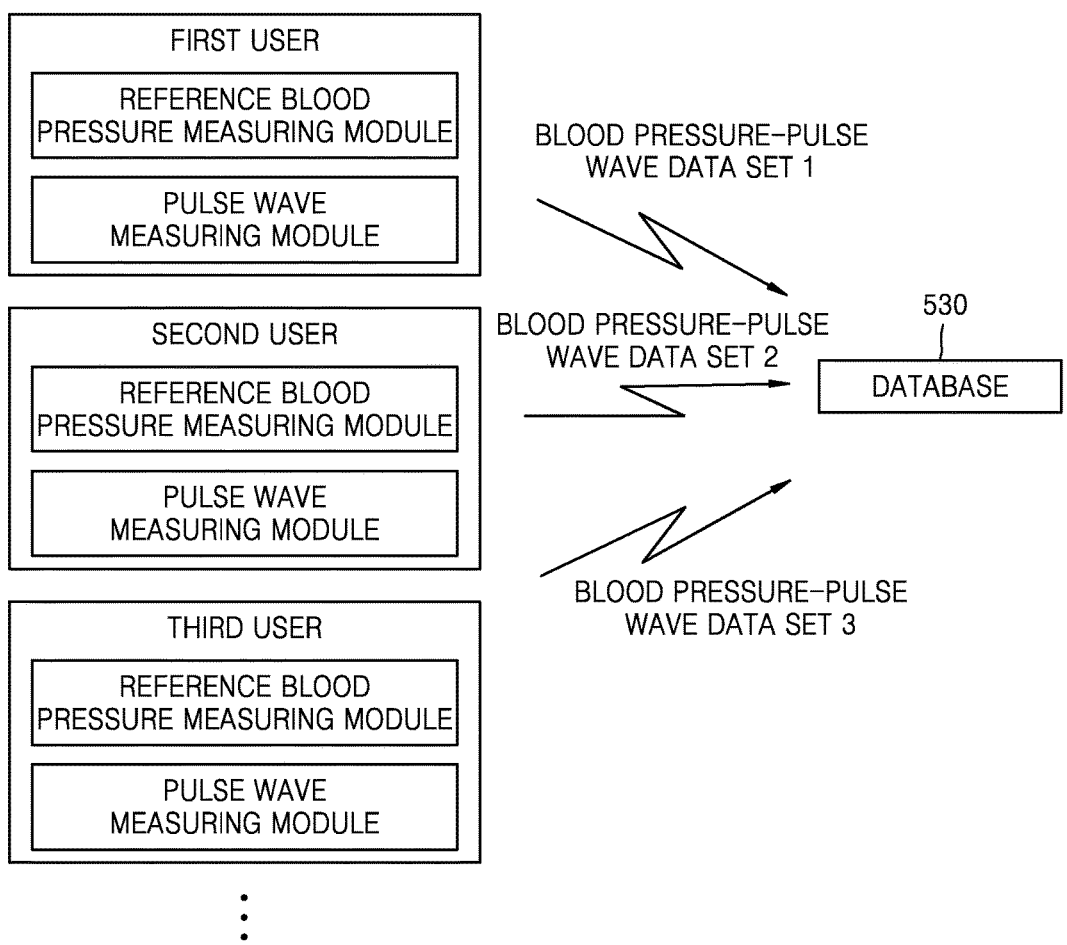
FIG. 6 is a diagram showing an example of updating a database of a calibration server.

FIG. 2 is a schematic block diagram showing a biometric information measuring system 1000 according to another exemplary embodiment. FIGS. 3A through 3C are diagrams showing examples of formation, shapes, and meanings of pulse waves measured by a biometric information measuring module 101 of the biometric information measuring system 1000. FIG. 4 is a diagram showing an example of biometric information that may be extracted from waveforms of pulse waves. FIG. 5 is a diagram showing pulse wave feature points that may be extracted from waveforms of pulse waves. FIG. 6 is a diagram showing an example of updating a database 530 of the calibration server 500.

First, referring to FIG. 2, the biometric information measuring system 1000 includes the biometric information measuring module 101 and the calibration server 500.

The biometric information measuring module 101 may include a pulse wave measuring module 110 that measures pulse waves of an target object OBJ, a biometric information analyzing module 120 that analyzes biometric information from pulse waves measured by the pulse wave measuring module 110, and a communication module 150 that communicates with the remote calibration server 500 to obtain calibration information used for biometric information analysis performed by the biometric information analyzing module 120. The biometric information measuring module 101 may also include a memory 130 and a user interface 140.

The pulse wave measuring module 110 includes a light emitter 112 and a light receiver 114. The light emitter 112 emits a light to the target object OBJ, and the light receiver 114 detects a light diffused or reflected by the target object OBJ. Pulse waves may be obtained from detected optical signals.

The target object OBJ is a target object for detecting biometric information, may be a biological portion that may contact or be adjacent to the pulse wave measuring module 110 of the biometric information measuring module 101, and may be a body part at which pulse waves may be easily measured via photoplethysmography (PPG). For example, the target object OBJ may be a portion of a wrist near a radial artery. When pulse waves are measured at a surface of a wrist of a position along which a radial artery extends, effects from external factors causing measurement errors, e.g., thickness of endothelium of the wrist, may be relatively small. Furthermore, a radial artery is a blood vessel for measuring blood pressure at a relatively high accuracy compared to other blood vessels in a wrist. However, the target object OBJ is not limited thereto and may be other body parts with a high blood vessel density, e.g., a finger, a toe, an earlobe, etc.

As shown in FIGS. 3A through 3C, traveling waves, which are generated by the heart and travel, and reflected waves, which are reflected by peripheral portions and travel back, constitute pulse waves by being overlapped with each other. Pulse waves are augmented as reflected waves overlap traveling waves. Since waveforms of pulse waves reflect cardiovascular system conditions and blood pressures, various information may be obtained via pulse wave analysis (PWA).

For example, FIG. 3A shows that as stiffness of a blood increases, the speed with which reflected waves arrive also increases, where arterial stiffness may be determined based on a transit time of reflected waves as an elastic artery, a stiff artery, etc. Furthermore, FIG. 3B shows that amplitudes of reflected waves are related to expansion and contraction of a blood vessel, and FIG. 3C shows factors related to heart-beat rates.

FIG. 4 illustrates examples of biometric information that may be extracted from waveforms of pulse waves based on overlapping and augmentation of traveling waves and reflected waves. For example, a pulse pressure (PP) is expressed as a difference between a systolic pressure and a diastolic pressure. A mean blood pressure is expressed as a diastolic pressure+PP/3 and may reflect cardiac loading. Furthermore, AP/PP represented as a percentage (%) indicates an augmentation index that may reflect elasticity of a blood vessel and load of the left ventricle. A reflective wave transit time (RWTT) may reflect hardness of a blood vessel. A subendocardial viability index (SERV) expressed as a diastolic area/systolic area may reflect conditions of a coronary artery, such as blood flow in the coronary artery or risk of coronary artery disease. Furthermore, myocardial contractile force may be measured by measuring an ejection time. Such indexes are related to diagnosis of a hypertension (determination of borderline hypertension), diagnosis of cardiac insufficiency (determination of systolic/diastolic dysfunctions), early diagnosis of cardiovascular system complications regarding diabetes, diagnosis of ischemic heart diseases, etc. and are indexes that may be clinically utilized for improving efficiency of medical prescriptions or treatments, where such indexes may only be obtained via invasive methods in the related art.

In consideration of such indexes, feature points may be extracted from waveforms of pulse waves as shown in FIG. 5. FIG. 5 shows feature points A, B, C, D, E, F, and G at locations related to the above descriptions, where more feature points may be added.

The biometric information analyzing module 120 may include a pulse wave feature point extracting module 122 that analyzes pulse waves measured by the pulse wave measuring module 110 and extracts designated feature points and a blood pressure calculator 124 that calculates a blood pressure by using a blood pressure estimating equation related to the feature points. The pulse wave feature point extracting module 122 may extract feature points as shown in FIG. 5. The blood pressure calculator 124 may calculate various biometric information by using the feature points. The blood pressure calculator 124 may receive a blood pressure estimating equation from the calibration server 500.

The calibration server 500 includes the database 530 having stored therein parameters regarding relationships between pulse waves and blood pressures and a blood pressure estimating equation calculator 510 that calculates the blood pressure estimating equation by using the database 530. The calibration server 500 also includes a communication module 550 to communicate with the biometric information measuring module 101.

The database 530 may include a set of data consisting of feature points of pulse waves and blood pressure values corresponding thereto. For example, the database 530 may be as shown below in Table 1.

TABLE 1

| A | B | C | D | Additional Feature Points (E, F, G . . .) | Y |
|---|---|---|---|---|---|
| 10 | 500 | 300 | 310 | . . . | 120 |
| 11 | 499 | 301 | 311 | . . . | 124 |
| 12 | 501 | 299 | 309 | . . . | 119 |
| . . . | . . . | . . . | . . . | . . . | . . . |

Here, Y is a value of blood pressure corresponding to the feature points and may be a blood pressure value which is directly measured.

From the database 530, a function f indicating a blood pressure estimating equation that defines Y=f(A, B, C, D, . . . ) may be modeled. For example, a regression analysis method or an artificial neural network method may be used therefor. Here, as the amount of data included in the database 530 increases, the accuracy of biometric information, such as a blood pressure, increases and may be analyzed from pulse waves.

Referring to FIG. 6, the database 530 and the calibration server 500 may be updated by a plurality of users. A plurality of users may be users using devices including pulse wave measuring modules and reference blood pressure measuring modules, and each of the devices may be a device with the biometric information measuring module 101 and a reference blood pressure measuring module, for example.

A reference blood pressure measuring module may be a device for directly measuring a blood pressure of a target object, e.g., a cuff-type blood pressure measuring device. A value corresponding to Y of Table 1 above may be obtained from a reference blood pressure measuring module. As described above, a pulse wave measuring module detects pulse waves by emitting a light to a target object and sensing a light reflected or diffused by the target object. Blood pressure-pulse wave data sets 1, 2, and 3 obtained from pulse waves measured by the pulse wave measuring module and blood pressures measured by the reference blood pressure measuring module are transmitted to the database 530, thereby updating the database 530. To this end, a device of each user may include a blood pressure-pulse wave data set extracting module for extracting parameters regarding relationships between pulse waves and blood pressures and a communication module for communication with the calibration server 500.

Referring back to FIG. 2, when the database 530 is updated, the blood pressure estimating equation calculator 510 of the calibration server 500 may update a blood pressure estimating equation. The biometric information measuring module 101 communicates with the calibration server 500 and may perform analysis of biometric information by using an updated blood pressure estimating equation.

The memory 130 may store programs for process and control of the biometric information analyzing module 120 and may store input/output data. For example, programs for the analysis of pulse waves and the calculation of blood pressure that are performed by the biometric information analyzing module 120 may be stored as executable code in the memory 130. Furthermore, measurement results obtained by the pulse wave measuring module 110 that are needed for operations performed by the biometric information analyzing module 120 may be stored in the memory 130.

The memory 130 may include at least one of storage media including a flash memory type storage medium, a multimedia card micro type storage medium, a card type memory (e.g., a SD memory or a XD memory), a random access memory (RAM), a static RAM (SRAM), a read-only memory (ROM), an electrically erasable-programmable ROM (EEPROM), a programmable ROM (PROM), a magnetic memory, a magnetic disk, and an optical disc.

The user interface 140 is an interface between the biometric information measuring module 101 and a user and/or a calibration server and/or other external devices and includes an input module and an output module. Here, a user may not only be an object for measuring biometric information, that is, the target object OBJ, but also be a person capable of using the biometric information measuring module 101, such as a medical expert. Information for operating the biometric information measuring module 101 may be input via the user interface 140 and a result of analysis may be output via the user interface 140. The user interface 140 may include a button, a connector, a keypad, and a display and may further include an acoustic output module or a vibration motor, for example.

The communication module 150 is arranged to received a blood pressure estimating equation to be used by the blood pressure calculator 124 from the calibration server 500. Furthermore, data used by the calibration server 500 to update a blood pressure estimating equation may be transmitted via the communication module 150. For example, data for updating the database 530 of the calibration server 500 may be transmitted via the communication module 150. Furthermore, results of analysis may be transmitted to other external devices via the communication module 150. For example, an external device may be a medical device using analyzed biometric information, a printer for printing out results of analysis, or a display device for displaying results of analysis. Furthermore, an external device may be a smart phone, a mobile phone, a personal digital assistant (PDA), a laptop PC, a desktop PC, or any of other mobile or non-mobile computing devices and is not limited thereto.

The communication module 150 may communicate with the calibration server 500 and other external devices via a Bluetooth communication, a Bluetooth Low Energy (BLE) communication, a near field communication (NFC) communication, a wireless LAN (WLAN) communication, a Zigbee communication, an infrared data association (IrDA) communication, a wi-fi direct (WFD) communication, a ultra wideband (UWB) communication, an Ant+ communication, or a Wi-Fi communication. However, the communication methods are not limited thereto.

The communication module 550 of the calibration server 500 may have a configuration similar to that of the communication module 150 of the biometric information measuring module 101.

The biometric information measuring module 101 may also be embodied in the form of a wearable device that may be worn by the target object OBJ. For example, the biometric information measuring module 101 may be embodied in the form of a wrist watch, a bracelet, or a wristband. Furthermore, the biometric information measuring module 101 may also be embodied in the form of a ring, an eyeglass, an earphone, or a headphone, but is not limited thereto.

Figure 7:
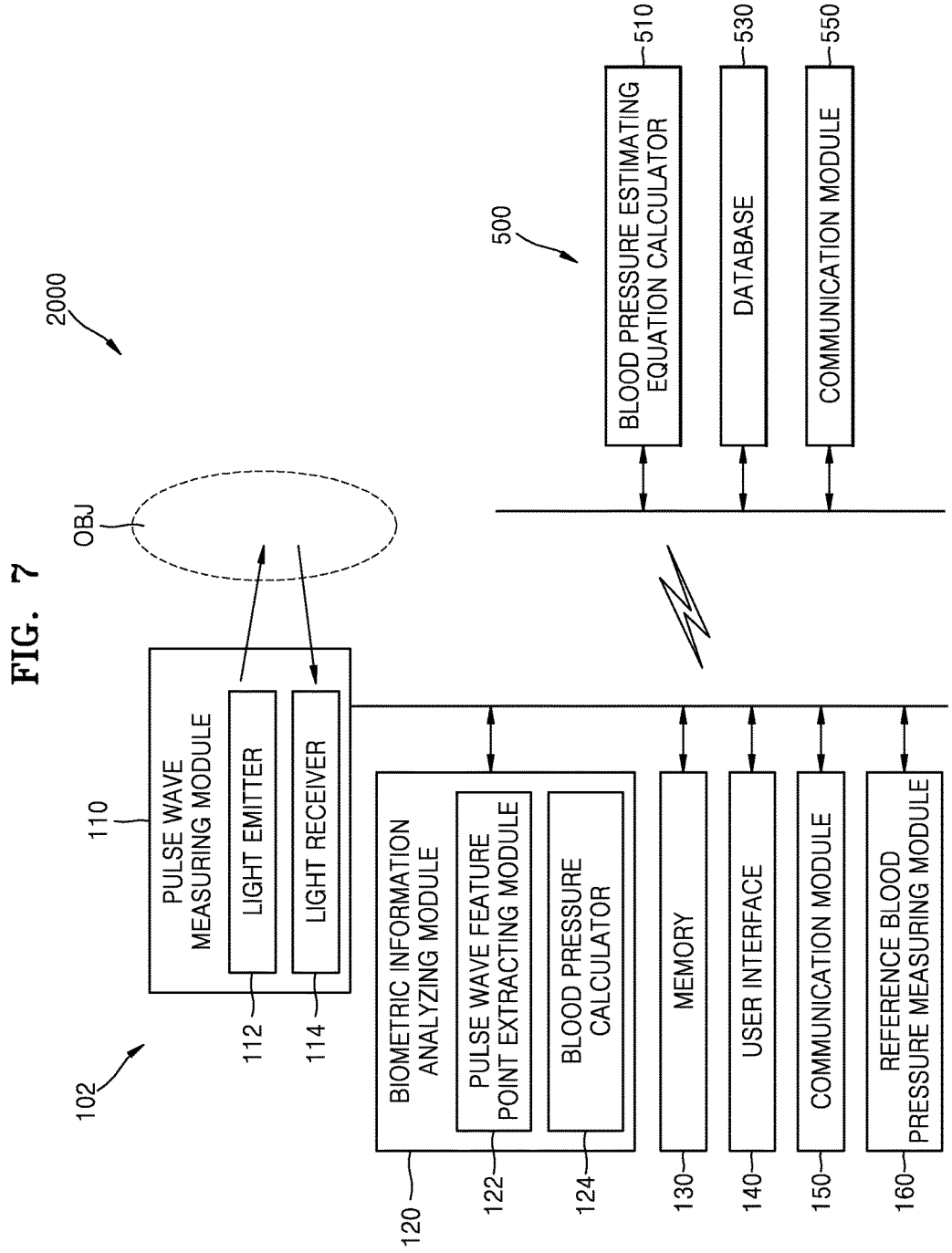
FIG. 7 is a schematic block diagram showing configuration of a biometric information measuring system according to another exemplary embodiment.

FIG. 7 is a schematic block diagram showing configuration of a biometric information measuring system 2000 according to another exemplary embodiment.

The biometric information measuring system 2000 includes a biometric information measuring module 102 and the calibration server 500. Other components of the biometric information measuring system 2000 are similar to those discussed above with respect to FIG. 2, and a redundant description thereof is omitted.

Unlike the biometric information measuring module 101, the biometric information measuring module 102 further includes a reference blood pressure measuring module 160. In other words, the biometric information measuring module 102 may not only use a blood pressure estimating equation of the calibration server 500 updated by other users, but also update a blood pressure estimating equation by transmitting results measured by the reference blood pressure measuring module 160 and the pulse wave measuring module 110 to the calibration server 500.

The reference blood pressure measuring module 160 may be a device for measuring a blood pressure of a target object using a direct method. For example, the reference blood pressure measuring module 160 may be a cuff-type blood pressure measuring device. The reference blood pressure measuring module 160 may be embodied as an individual module that may be separated from the biometric information measuring module 102. For example, components including the pulse wave measuring module 110, the biometric information analyzing module 120, and the communication module 150 may be arranged in a main body, whereas the reference blood pressure measuring module 160 may be embodied as a module that may be connected to the main body via a wire or wirelessly. The main body may be embodied in the form of a wearable device that may be worn by the target object OBJ.

In a general measurement mode, the biometric information measuring module 102 may be used while the reference blood pressure measuring module 160 is not connected to the main body, and biometric information may be analyzed by using pulse waves measured by the pulse wave measuring module 110 and a blood pressure estimating equation received from the calibration server 500.

In a calibration mode, the reference blood pressure measuring module 160 may be connected to the main body to update the database 530 of the calibration server 500. In other words, after pulse waves are measured by the pulse wave measuring module 110 and a blood pressure is measured by the reference blood pressure measuring module 160, blood pressure-pulse wave data sets may be transmitted to the calibration server 500. To this end, the biometric information measuring system 2000 may further include a blood pressure-pulse wave data set extracting module that may extract parameters regarding relationships between pulse waves and blood pressures from pulse waves measured by the pulse wave measuring module 110 and blood pressures measured by the reference blood pressure measuring module 160.

Figure 8:
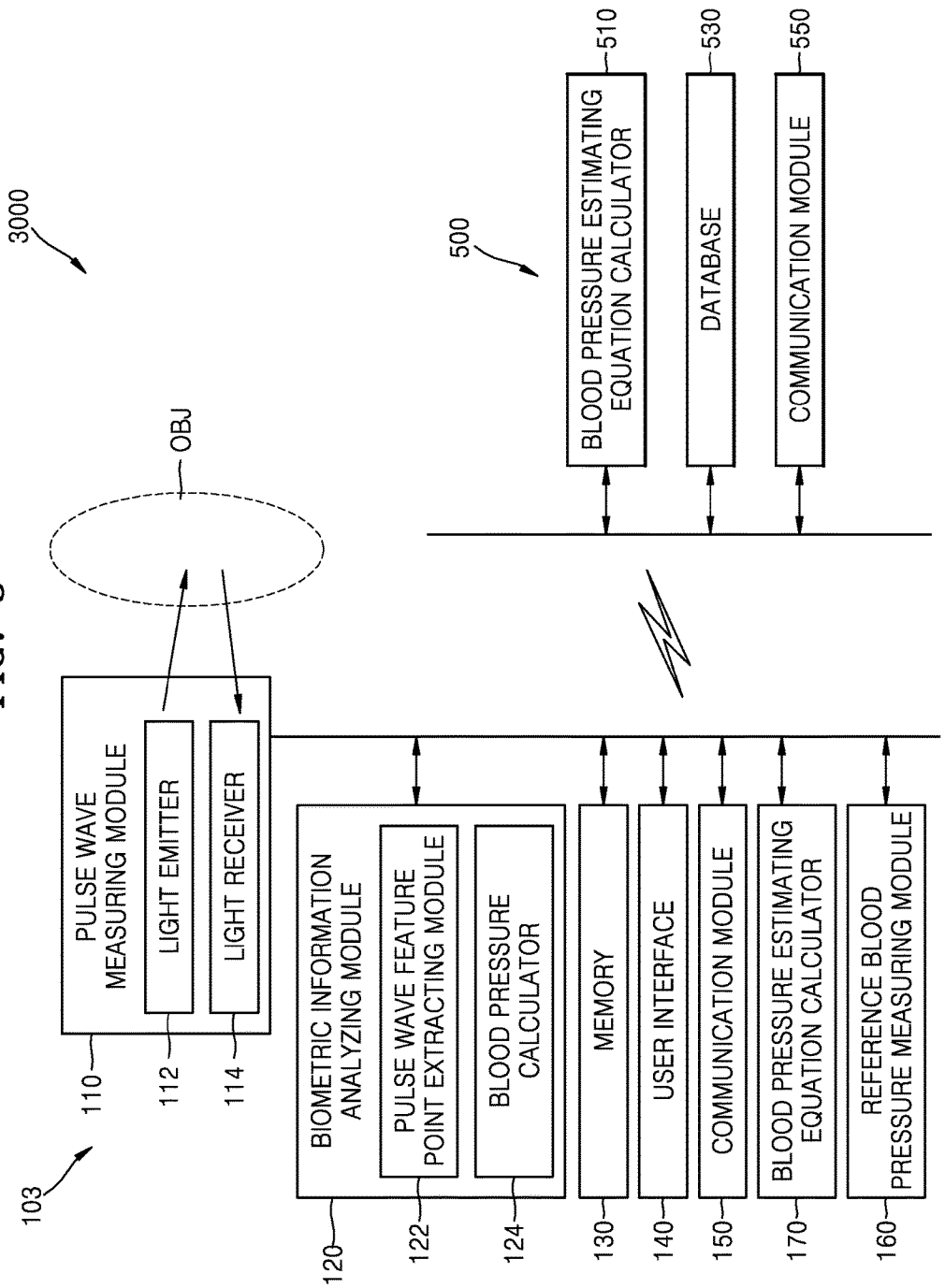
FIG. 8 is a schematic block diagram showing configuration of a biometric information measuring system according to another exemplary embodiment.

FIG. 8 is a schematic block diagram showing configuration of a biometric information measuring system 3000 according to another exemplary embodiment.

The biometric information measuring system 3000 includes a biometric information measuring module 103 and the calibration server 500. Other components of the biometric information measuring system 2000 are similar to those discussed above with respect to FIG. 2, and a redundant description thereof is omitted.

Unlike the biometric information analyzing module 120 of FIG. 7, the biometric information measuring module 103 further includes a blood pressure estimating equation calculator 170.

The memory 130 of the biometric information measuring module 102 may not only store programs for process and control of the biometric information analyzing module 120, input/output data, and programs for pulse wave analysis and blood pressure calculation, but also store a local database having stored therein parameters regarding relationships between pulse waves and blood pressures. Furthermore, the biometric information measuring module 103 may further include a blood pressure-pulse wave data set extracting module that may extract parameters regarding relationships between pulse waves and blood pressures from pulse waves measured by the pulse wave measuring module 110 and blood pressures measured by the reference blood pressure measuring module 160.

The biometric information measuring module 103 according to the present exemplary embodiment may not only receive a blood pressure estimating equation from the calibration server 500 and analyze pulse waves measured by the pulse wave measuring module 110 by using the same, but also calculate a blood pressure estimating equation by using the reference blood pressure measuring module 160 arranged at the biometric information measuring module 103 as an occasion demands.

The blood pressure estimating equation calculator 170 may calculate a blood pressure estimating equation by using a local database. Furthermore, the local database may be updated by reflecting results measured by the reference blood pressure measuring module 160. In other words, parameters regarding relationships between pulse waves and blood pressures are extracted by a blood pressure-pulse wave data set extracting module from results measured by the pulse wave measuring module 110 and the reference blood pressure measuring module 160 arranged at the biometric information measuring module 103, and the local database may be updated by reflecting the parameters regarding relationships between pulse waves and blood pressures. The local database may also be updated by receiving the database 530 of the calibration server 500. The blood pressure estimating equation calculator 170 may calculate a blood pressure estimating equation by receiving the database 530 of the calibration server 500.

Figure 9:
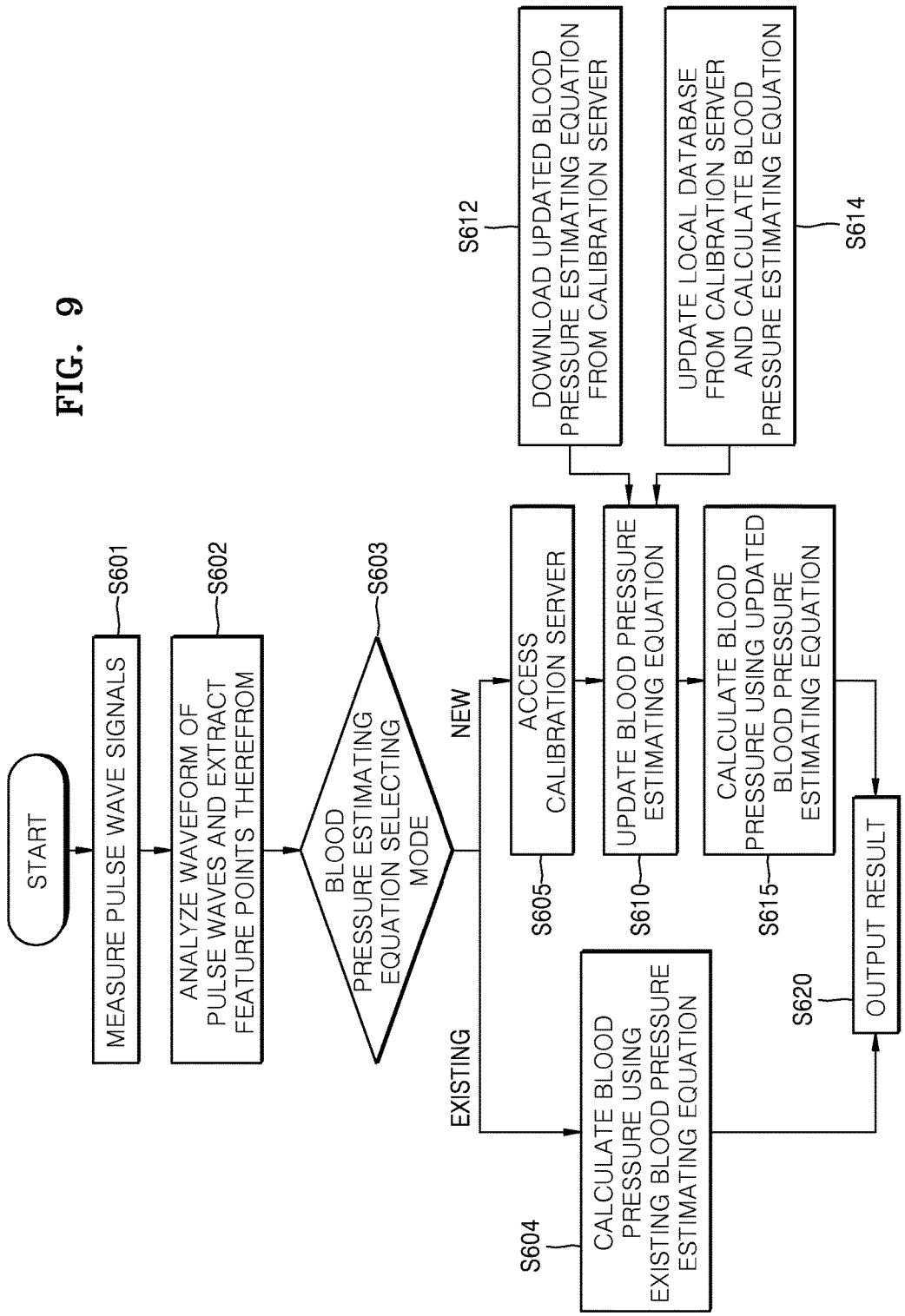
FIG. 9 is a flowchart showing a method of measuring biometric information according to an exemplary embodiment.

FIG. 9 is a flowchart showing a method of measuring biometric information according to an exemplary embodiment.

The method of measuring biometric information according to the present exemplary embodiment may be performed by using one from among the biometric information measuring system 1, 1000, 2000, and 3000 described above.

The biometric information measuring system 1, 1000, 2000, and 3000 may measure pulse wave signals (operation S601), and then analyze waveforms of the pulse wave signals and extract feature points from the waveforms (operation S602). Thereafter, the biometric information measuring system 1, 1000, 2000, and 3000 may select a blood pressure estimating equation (operation S603). However, the sequence or order of the operations S601, S602, and S603 is merely an example, and the operation S603 for selecting a blood pressure estimating equation may be performed first.

In the operation S603, the biometric information measuring system 1, 1000, 2000, and 3000 may determine whether an existing blood pressure estimating equation or a newly updated blood pressure estimating equation is to be used. When the newly updated blood pressure estimating equation is determined to be used, the biometric information measuring system 1, 1000, 2000, and 3000 may access a calibration server 500 (operation S605) and update a blood pressure estimating equation which is stored in the biometric information measuring system 1, 1000, 2000, and 3000 (operation S610). To update the blood pressure estimating equation, an updated blood pressure estimating equation may be downloaded from the calibration server 500 (operation S612). Alternatively, a new blood pressure estimating equation may be calculated by updating a local database based on a database of the calibration server 500 (operation S614). Next, a blood pressure is calculated by using the updated or new blood pressure estimating equation (operation S615), and a result value of the blood pressure is output (operation S620).

In case of using an existing blood pressure estimating equation, the biometric information measuring system 1, 1000, 2000, and 3000 may not access the calibration server 500. Blood pressure is calculated by using a blood pressure estimating equation that was most recently used and stored (operation S604), and a result value of the blood pressure is output (operation S620).

Figure 10:
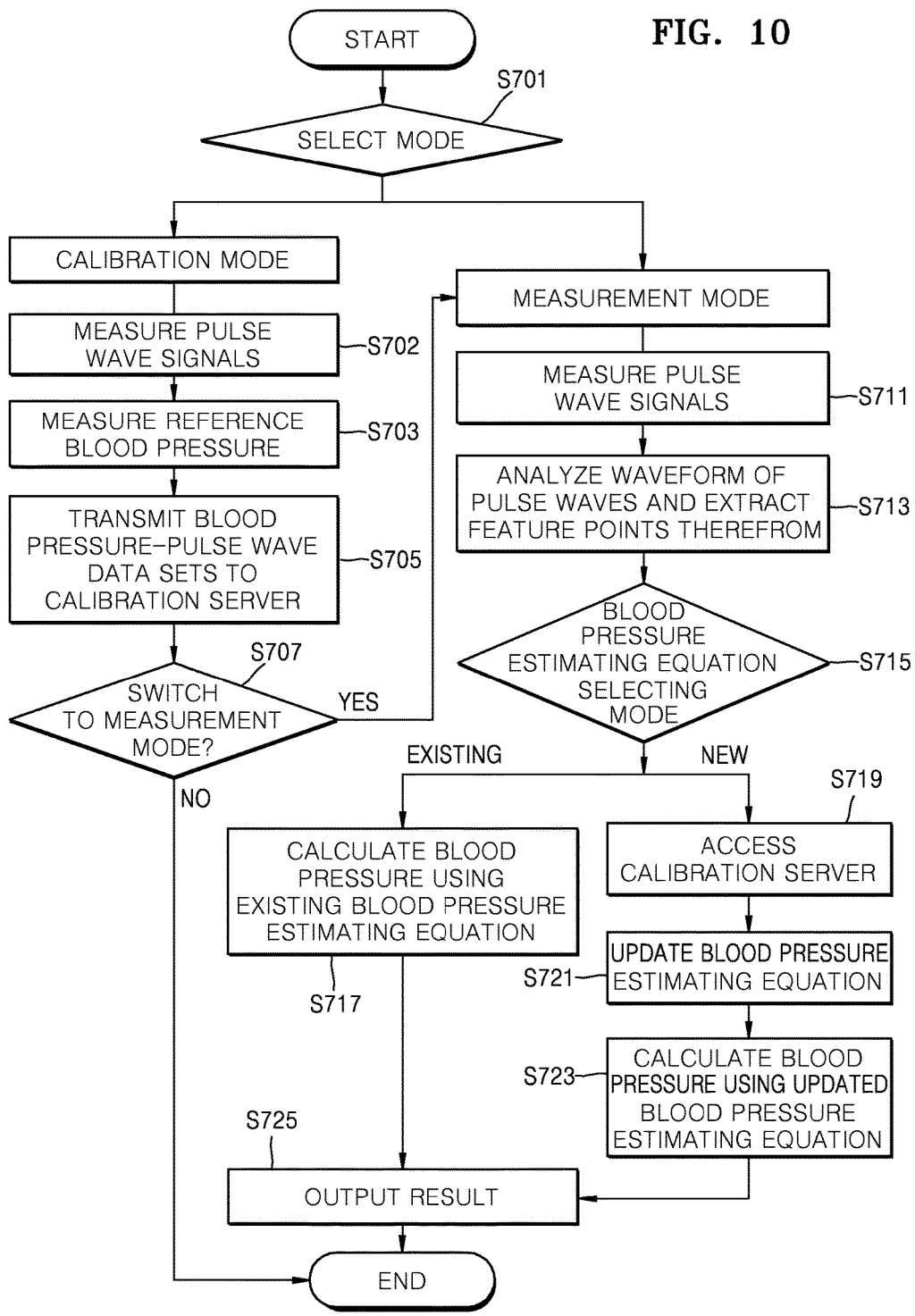
FIG. 10 is a flowchart showing a method of measuring biometric information according to another exemplary embodiment.

FIG. 10 is a flowchart showing a method of measuring biometric information according to another exemplary embodiment.

The method of measuring biometric information according to the present exemplary embodiment utilizes a biometric information measuring device including a reference blood pressure measuring module and may be performed by using one of the biometric information measuring system 1, 1000, and 2000 described above.

In operation S701, a calibration mode or a measurement mode is selected.

If the measurement mode is selected, pulse wave signals are measured (operation S711), waveforms of pulse waves are analyzed, feature points are extracted from pulse waves (operation S713), and then a blood pressure estimating equation may be selected (operation S715). However, the sequence is merely an example, and the operation S715 may be performed before the operation S711 or the operation S713.

In the operation S715 for selecting a blood pressure estimating equation, it is determined to use either an existing an existing blood pressure estimating equation or a newly updated blood pressure estimating equation. In case of using the newly updated blood pressure estimating equation, a calibration server 500 is accessed (operation S719) and a blood pressure estimating equation of the biometric information measuring system 1, 1000, 2000, and 3000 is updated (operation S721). To update the blood pressure estimating equation, an updated blood pressure estimating equation may be downloaded from the calibration server 500 as described above with reference to FIG. 9. Alternatively, a new blood pressure estimating equation may be calculated by updating a local database based on a database of the calibration server as described above with reference to FIG. 9. Next, a blood pressure is calculated by using the updated blood pressure estimating equation (operation S717), and a result value of the blood pressure is output (operation S725).

In case of using an existing blood pressure estimating equation, it may be unnecessary to access the calibration server 500. A blood pressure is calculated by using a blood pressure estimating equation that is most recently used and stored (operation S717), and a result value of the blood pressure is output (operation S725).

If the calibration mode is selected, pulse wave signals are measured (operation S702), and a reference blood pressure is measured (operation S703). However, the sequence is merely an example and may be reversed. Results of measuring pulse waves and a result of measuring a reference blood pressure are transmitted to a calibration server (operation S705).

Next, based on a selection to switch to the measurement mode (operation S707), the measurement mode may be performed.

For measuring and analyzing biometric information using the above described biometric information measuring devices, biometric information measuring systems, and biometric information measuring methods, it is described above that at least some of a plurality of users update information stored in a calibration server and a plurality of users receive and use updated calibration information in terms of relationships between pulse waves and blood pressures. However, other embodiments may also be applied to analysis of various biometric information of which accuracy may be improved by updating calibration information based on data provided by a plurality of users.

As described above, according to the one or more of the above exemplary embodiments, a plurality of users using biometric information measuring devices may update calibration information stored in a calibration server, and thus the calibration server may provide up-to-date calibration information to the biometric information measuring devices.

The biometric information measuring device may communicate with the calibration server, receive up-to-date calibration information, and utilize the calibration information for analyzing biometric information. Therefore, accuracy of biometric information analysis may be improved.

While not restricted thereto, an exemplary embodiment can be embodied as computer-readable code on a computer-readable recording medium. The computer-readable recording medium is any data storage device that can store data that can be thereafter read by a computer system. Examples of the computer-readable recording medium include read-only memory (ROM), random-access memory (RAM), CD-ROMs, magnetic tapes, floppy disks, and optical data storage devices. The computer-readable recording medium can also be distributed over network-coupled computer systems so that the computer-readable code is stored and executed in a distributed fashion. Also, an exemplary embodiment may be written as a computer program transmitted over a computer-readable transmission medium, such as a carrier wave, and received and implemented in general-use or special-purpose digital computers that execute the programs. Moreover, it is understood that in exemplary embodiments, one or more modules of the above-described apparatuses and devices can include circuitry, a processor, a microprocessor, etc., and may execute a computer program stored in a computer-readable medium.

The foregoing exemplary embodiments are merely exemplary and are not to be construed as limiting. The present teaching can be readily applied to other types of apparatuses. Also, the description of the exemplary embodiments is intended to be illustrative, and not to limit the scope of the claims, and many alternatives, modifications, and variations will be apparent to those skilled in the art.

What is claimed is:

1. A biometric information measuring device comprising:
a pulse wave measuring module comprising a light emitter and a light receiver to measure pulse waves of a target subject;
a communication interface configured to receive, from a remote calibration server, a blood pressure estimating equation that is updated by the remote calibration server, based on calibration information extracted from blood pressure pulse waves of a plurality of subjects, the calibration information comprising a pulse pressure (PP) expressed as a difference between a systolic pressure and a diastolic pressure of the plurality of subjects, a sum of the diastolic pressure and one third of the PP, and an augmented pressure (AP) divided by the PP; and
at least one processor configured to determine a blood pressure of the target subject based on feature points of the measured pulse waves and the updated blood pressure estimating equation,
wherein the calibration server is configured to communicate with another device including a pulse wave measurer and a blood pressure measurer and update the calibration information based on results measured by the another device, the results including a set of a pulse wave and a blood pressure.

2. The biometric information measuring device of claim 1, wherein the calibration server is further configured to calculate the blood pressure estimating equation by using a database that stores parameters regarding relationships between reference pulse waves and reference blood pressures.

3. The biometric information measuring device of claim 2, further comprising a cuff-type blood pressure monitor configured to directly measure a blood pressure of a target object.

4. The biometric information measuring device of claim 3, wherein the at least one processor is further configured to extract parameters regarding relationships between pulse waves and blood pressures from the pulse waves measured by the pulse wave measuring module and the blood pressure measured by the cuff-type blood pressure monitor.

5. The biometric information measuring device of claim 4, wherein the calibration server is further configured to receive the extracted parameters and update the database.

6. The biometric information measuring device of claim 3, further comprising a local database in which the parameters regarding the relationships between the reference pulse waves and the reference blood pressures are stored.

7. The biometric information measuring device of claim 6, the at least one processor is further configured to update the local database with the extracted parameters and calculate the blood pressure estimating equation by using the updated local database.

8. The biometric information measuring device of claim 7, wherein the at least one processor is further configured to receive data of the database in the calibration server to update the local database, and further update the updated blood pressure estimating equation by using the updated local database.

9. The biometric information measuring device of claim 3, wherein the pulse wave measuring module, the at least one processor, and the communication interface are arranged in a main body of the biometric information measuring device, and
the cuff-type blood pressure monitor is connectable to the main body.

10. The biometric information measuring device of claim 9, wherein the calibration information further comprises a reflective wave transmit time (RWTT) that indicates hardness of a blood vessel of the plurality of subjects.

11. The biometric information measuring device of claim 1, wherein the calibration information further comprises a subendocardial viability index (SERV) that corresponds to a diastolic area divided by a systolic area, and indicates a blood flow rate of the plurality of subjects.

12. A biometric information measuring system comprising:
a calibration server configured to update a blood pressure estimating equation used for analyzing biometric information of a target subject, based on calibration information extracted from blood pressure pulse waves of a plurality of subjects, the calibration information comprising a pulse pressure (PP) expressed as a difference between a systolic pressure and a diastolic pressure of the plurality of subjects, a sum of the diastolic pressure and one third of the PP, and an augmented pressure (AP) divided by the PP;
a biometric information measuring device comprising:
a pulse wave measuring module that comprises a light emitter and a light receiver to measure pulse waves of the target subject;
a communication interface configured to obtain the calibration information from the calibration server; and
at least one processor configured to determine a blood pressure of the target subject based on feature points of the pulse waves and the updated blood pressure estimating equation; and
another device including a pulse wave measurer and a blood pressure measurer,
wherein the calibration server is configured to communicate with the another device and update the calibration information based on results measured by the another device, the results including a set of a pulse wave and a blood pressure.

13. The biometric information measuring system of claim 12, wherein the calibration server is further configured to calculate the blood pressure estimating equation by using a database that stores parameters regarding relationships between reference pulse waves and reference blood pressures.

14. The biometric information measuring system of claim 13, further comprising a cuff-type blood pressure monitor configured to directly measure the blood pressure of the target subject.

15. The biometric information measuring device of claim 14, wherein the at least one processor is configured to extract parameters regarding a relationship between the blood pressure determined by the pulse wave measuring module and the blood pressure measured by the cuff-type blood pressure monitor.

16. The biometric information measuring system of claim 14, wherein the pulse wave measuring module, the at least one processor, and the communication interface are arranged in a main body of the biometric information measuring device, and
the cuff-type blood pressure monitor is connected to the main body.

* * * * *